(12) United States Patent
Hansell et al.

(10) Patent No.: US 10,130,490 B2
(45) Date of Patent: *Nov. 20, 2018

(54) INTERVERTEBRAL SPACER (71) Applicant: GLOBUS MEDICAL, INC., Audubon, PA (US)

(72) Inventors: Noah Hansell, King of Prussia, PA (US); Marcin Niemiec, Norristown, PA (US); William S. Rhoda, Media, PA (US); Michael Meccariello, Phoenixville, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/695,593

(22) Filed: Sep. 5, 2017

(65) Prior Publication Data
US 2017/0360574 A1 Dec. 21, 2017

Related U.S. Application Data (63) Continuation of application No. 14/683,502, filed on Apr. 10, 2015, now Pat. No. 9,782,269, which is a (Continued)

(51) Int. Cl.
*A61F 2/44* (2006.01)
*A61F 2/46* (2006.01)
*A61B 90/00* (2016.01)
*A61F 2/30* (2006.01)

(52) U.S. Cl.
CPC ............ *A61F 2/4465* (2013.01); *A61B 90/39* (2016.02); *A61F 2/4611* (2013.01);
(Continued)

(58) Field of Classification Search
CPC ........ A61F 2/4601; A61F 2/4611; A61F 2/44; A61F 2/4455; A61F 2/446; A61F 2/4465;
(Continued)

(56) References Cited

U.S. PATENT DOCUMENTS 5,562,736 A 10/1996 Ray et al.
5,607,424 A 3/1997 Tropiano
(Continued)

FOREIGN PATENT DOCUMENTS

EP 1925271 B1 8/2009
WO 2006079356 A1 8/2006
WO 2010075555 A2 7/2010

*Primary Examiner* — Alvin Stewart (57) ABSTRACT

Disclosed is an assembly and method for implant installation between adjacent vertebral bodies of a patient. The implant has a support body and a rotatable insert therein and the support body is curved for installation between adjacent vertebral bodies transforaminally. An installation instrument is also disclosed for removable attachment to implant and engagement with the rotatable insert to selectively permit rotation between the insert and the support body. The installation instrument extends along a longitudinal tool axis and when the installation instrument is in a first position the insert is rotationally fixed with respect to the support body and when the installation instrument is in a second position the support body may rotate with respect to the insert.

16 Claims, 9 Drawing Sheets

Related U.S. Application Data continuation of application No. 13/406,663, filed on Feb. 28, 2012, now Pat. No. 9,138,330, which is a continuation of application No. 12/250,168, filed on Oct. 13, 2008, now Pat. No. 8,147,554.

(52) U.S. Cl.
CPC ... *A61F 2/30734* (2013.01); *A61F 2002/3008* (2013.01); *A61F 2002/3082* (2013.01); *A61F 2002/30131* (2013.01); *A61F 2002/30364* (2013.01); *A61F 2002/30365* (2013.01); *A61F 2002/30538* (2013.01); *A61F 2002/30594* (2013.01); *A61F 2002/30616* (2013.01); *A61F 2002/30622* (2013.01); *A61F 2002/30785* (2013.01); *A61F 2002/30843* (2013.01); *A61F 2002/30904* (2013.01); *A61F 2002/4475* (2013.01); *A61F 2002/4627* (2013.01); *A61F 2002/4629* (2013.01); *A61F 2220/0033* (2013.01); *A61F 2230/0013* (2013.01); *A61F 2250/0006* (2013.01); *A61F 2250/0098* (2013.01)

(58) Field of Classification Search
CPC .............. A61F 2/30; A61F 2002/30131; A61F 2002/30133; A61F 2002/30364; A61F 2002/30365
See application file for complete search history.

(56) References Cited

U.S. PATENT DOCUMENTS

| | | | |
|---|---|---|---|
| 5,609,636 A | 3/1997 | Kohrs et al. | |
| 5,658,336 A | 8/1997 | Pisharodi | |
| 5,716,415 A | 2/1998 | Steffee | |
| 5,716,416 A | 2/1998 | Lin | |
| 5,766,252 A | 6/1998 | Henry et al. | |
| 5,824,093 A | 10/1998 | Ray et al. | |
| 5,885,287 A | 3/1999 | Bagby | |
| 6,033,438 A | 3/2000 | Bianchi et al. | |
| 6,080,155 A | 6/2000 | Michelson | |
| 6,179,875 B1 | 1/2001 | Von Strempel | |
| 6,183,517 B1 | 2/2001 | Suddaby | |
| 6,183,518 B1 | 2/2001 | Ross et al. | |
| 6,224,607 B1 | 5/2001 | Michelson | |
| 6,368,351 B1 | 4/2002 | Glenn et al. | |
| 6,375,655 B1 | 4/2002 | Zdeblick et al. | |
| 6,387,130 B1 | 5/2002 | Stone et al. | |
| 6,749,635 B1 | 6/2004 | Bryan | |
| 6,761,738 B1 | 7/2004 | Boyd | |
| 6,761,739 B2 | 7/2004 | Shepard | |
| 6,764,514 B1 | 7/2004 | Li et al. | |
| 6,802,863 B2 | 10/2004 | Lawson et al. | |
| 6,830,570 B1 | 12/2004 | Frey et al. | |
| 6,830,589 B2 | 12/2004 | Erickson | |
| 6,852,129 B2 | 2/2005 | Gerbec et al. | |
| 6,875,213 B2 | 4/2005 | Michelson | |
| 6,881,228 B2 | 4/2005 | Zdeblick et al. | |
| 6,936,071 B1 | 8/2005 | Marnay et al. | |
| 6,942,698 B1 | 9/2005 | Jackson | |
| 6,986,789 B2 | 1/2006 | Schultz et al. | |
| 7,056,344 B2 | 6/2006 | Huppert et al. | |
| 7,060,096 B1 | 6/2006 | Schopf et al. | |
| 7,118,599 B2 | 10/2006 | Errico | |
| 7,125,425 B2 | 10/2006 | Foley | |
| 7,147,665 B1 | 12/2006 | Bryan et al. | |
| 7,204,851 B2 | 4/2007 | Trieu et al. | |
| 7,204,852 B2 | 4/2007 | Marnay et al. | |
| 7,207,991 B2 | 4/2007 | Michelson | |
| 7,217,291 B2 | 5/2007 | Zucherman et al. | |
| 7,223,292 B2 | 5/2007 | Messerli et al. | |
| 7,226,483 B2 | 6/2007 | Gerber et al. | |
| 7,232,463 B2 | 6/2007 | Falahee | |
| 7,250,060 B2 | 7/2007 | Trieu | |
| 7,255,698 B2 | 8/2007 | Michelson | |
| 7,288,093 B2 | 10/2007 | Michelson | |
| 7,331,995 B2 | 2/2008 | Eisermann et al. | |
| 7,331,996 B2 | 2/2008 | Sato et al. | |
| 7,361,193 B2 | 4/2008 | Frey et al. | |
| 7,481,840 B2 | 1/2009 | Zucherman et al. | |
| 7,503,935 B2 | 3/2009 | Zucherman et al. | |
| 7,575,600 B2 | 8/2009 | Zucherman et al. | |
| 7,611,538 B2 | 11/2009 | Belliard et al. | |
| 7,621,958 B2 | 11/2009 | Paul et al. | |
| 7,708,780 B2 | 5/2010 | Zubok et al. | |
| 7,771,479 B2 | 8/2010 | Humphreys et al. | |
| 7,776,093 B2 | 8/2010 | Wolek et al. | |
| 7,803,162 B2 | 9/2010 | Marnay et al. | |
| 7,896,919 B2 | 3/2011 | Belliard et al. | |
| 8,147,554 B2 * | 4/2012 | Hansell ................. | A61F 2/4611 623/17.16 |
| D665,081 S * | 8/2012 | Hansell ................. | A61F 2/4465 D24/155 |
| 8,506,629 B2 * | 8/2013 | Weiland ................ | A61F 2/4465 623/17.11 |
| 9,138,330 B2 * | 9/2015 | Hansell ................. | A61F 2/4611 |
| 9,782,269 B2 * | 10/2017 | Hansell ................. | A61F 2/4465 |
| 2004/0024462 A1 | 2/2004 | Ferree et al. | |
| 2004/0172135 A1 | 9/2004 | Mitchell | |
| 2005/0033435 A1 | 2/2005 | Belliard et al. | |
| 2005/0065611 A1 | 3/2005 | Huppert et al. | |
| 2005/0143824 A1 | 6/2005 | Richelsoph et al. | |
| 2005/0154462 A1 | 7/2005 | Zucherman et al. | |
| 2005/0159818 A1 | 7/2005 | Blain | |
| 2005/0228500 A1 | 10/2005 | Kim et al. | |
| 2005/0234555 A1 | 10/2005 | Sutton et al. | |
| 2005/0267581 A1 | 12/2005 | Marnay et al. | |
| 2005/0283245 A1 | 12/2005 | Gordon et al. | |
| 2006/0004453 A1 | 1/2006 | Bartish et al. | |
| 2006/0069439 A1 | 3/2006 | Zucherman et al. | |
| 2006/0069440 A1 | 3/2006 | Zucherman et al. | |
| 2006/0069441 A1 | 3/2006 | Zucherman et al. | |
| 2006/0116769 A1 | 6/2006 | Marney et al. | |
| 2006/0229627 A1 * | 10/2006 | Hunt ................. | A61B 17/1659 606/86 R |
| 2006/0235426 A1 | 10/2006 | Lim et al. | |
| 2006/0241761 A1 | 10/2006 | Gately | |
| 2007/0043359 A1 | 2/2007 | Altarac et al. | |
| 2007/0073405 A1 | 3/2007 | Verhulst et al. | |
| 2007/0118223 A1 | 5/2007 | Allard et al. | |
| 2007/0173942 A1 | 7/2007 | Heinz et al. | |
| 2007/0225808 A1 * | 9/2007 | Warnick ................. | A61F 2/4465 623/17.11 |
| 2008/0009880 A1 * | 1/2008 | Warnick ................. | A61F 2/4455 606/99 |
| 2008/0065082 A1 | 3/2008 | Chang et al. | |
| 2008/0091211 A1 * | 4/2008 | Gately ................. | A61B 17/1671 606/99 |
| 2008/0140085 A1 * | 6/2008 | Gately ................. | A61F 2/4465 606/99 |
| 2008/0221694 A1 * | 9/2008 | Warnick ................. | A61F 2/4465 623/17.16 |
| 2008/0294259 A1 | 11/2008 | De Villiers et al. | |
| 2009/0005874 A1 | 1/2009 | Fleischmann et al. | |
| 2009/0018663 A1 | 1/2009 | Cook et al. | |
| 2009/0192616 A1 | 7/2009 | Zielinski | |
| 2009/0254183 A1 | 10/2009 | Humphreys et al. | |
| 2009/0276049 A1 * | 11/2009 | Weiland ................ | A61F 2/4465 623/17.16 |
| 2010/0004746 A1 | 1/2010 | Arramon | |
| 2010/0004752 A1 | 1/2010 | White et al. | |
| 2010/0030336 A1 | 2/2010 | Cope | |
| 2010/0094422 A1 | 4/2010 | Hansell | |
| 2010/0191337 A1 * | 7/2010 | Zamani ................. | A61F 2/4465 623/17.16 |
| 2011/0270402 A1 | 11/2011 | Frey et al. | |
| 2011/0276141 A1 | 11/2011 | Caratsch | |
| 2011/0276142 A1 | 11/2011 | Niemiec et al. | |

* cited by examiner

INTERVERTEBRAL SPACER

CROSS REFERENCE TO RELATED APPLICATIONS

This Patent Application is a continuation application claiming priority to U.S. patent application Ser. No. 14/683,502, filed Apr. 10, 2015 which is a continuation application claiming priority to U.S. patent application Ser. No. 13/406,663, filed Feb. 28, 2012, now issued as U.S. Pat. No. 9,138,330, which is a continuation application claiming priority to U.S. patent application Ser. No. 12/250,168 filed on Oct. 13, 2008, now issued as U.S. Pat. No. 8,147,554. Each of these references is hereby incorporated by reference herein in its entirety.

FIELD OF THE INVENTION

The present invention generally relates to intervertebral spacers for fusing vertebral bodies. In particular, certain embodiments are directed to an intervertebral spacer configured and dimensioned to be implanted transforaminally.

BACKGROUND OF THE INVENTION

The vertebrate spine is the axis of the skeleton providing structural support for the other body parts. In humans, the normal spine has seven cervical, twelve thoracic and five lumbar segments. The lumbar spine sits upon the sacrum, which then attaches to the pelvis, and in turn is supported by the hip and leg bones. The bony vertebral bodies of the spine are separated by intervertebral discs, which act as joints but allow known degrees of flexion, extension, lateral bending, and axial rotation.

The typical vertebra has a thick anterior bone mass called the vertebral body, with a neural (vertebral) arch that arises from the posterior surface of the vertebral body. The centra of adjacent vertebrae are supported by intervertebral discs. Each neural arch combines with the posterior surface of the vertebral body and encloses a vertebral foramen. The vertebral foramina of adjacent vertebrae are aligned to form a vertebral canal, through which the spinal sac, cord and nerve rootlets pass. The portion of the neural arch which extends posteriorly and acts to protect the spinal cord's posterior side is known as the lamina. Projecting from the posterior region of the neural arch is the spinous process.

The intervertebral disc primarily serves as a mechanical cushion permitting controlled motion between vertebral segments of the axial skeleton. The normal disc is a unique, mixed structure, comprised of three component tissues: the nucleus pulpous ("nucleus"), the annulus fibrosus ("annulus") and two vertebral end plates. The two vertebral end plates are composed of thin cartilage overlying a thin layer of hard, cortical bone which attaches to the spongy, richly vascular, cancellous bone of the vertebral body. The end plates thus act to attach adjacent vertebrae to the disc. In other words, a transitional zone is created by the end plates between the malleable disc and the bony vertebrae.

The spinal disc and/or vertebral bodies may be displaced or damaged due to trauma, disease, degenerative defects, or wear over an extended period of time. One result of this displacement or damage to a spinal disc or vertebral body may be chronic back pain.

A disc herniation occurs when the annulus fibers are weakened or torn and the inner tissue of the nucleus becomes permanently bulged, distended, or extruded out of its normal, internal annulus confines. The mass of a herniated or "slipped" nucleus tissue can compress a spinal nerve, resulting in leg pain, loss of muscle control, or even paralysis. Alternatively, with discal degeneration, the nucleus loses its water binding ability and deflates, as though the air had been let out of a tire. Subsequently, the height of the nucleus decreases causing the annulus to buckle in areas where the laminated plies are loosely bonded. As these overlapping laminated plies of the annulus begin to buckle and separate, either circumferential or radial annular tears may occur, which may contribute to persistent or disabling back pain. Adjacent, ancillary spinal facet joints will also be forced into an overriding position, which may create additional back pain.

Whenever the nucleus tissue is herniated or removed by surgery, the disc space will narrow and may lose much of its normal stability. In many cases, to alleviate back pain from degenerated or herniated discs, the disc is removed along with all or part of at least one neighboring vertebrae and is replaced by an implant that promotes fusion of the remaining bony anatomy.

While this treatment may help alleviate the pain once the vertebrae have been successfully fused together, there remains the possibility that the surgical procedure may not successfully or fully bring about the intended fusion. The success or failure of spinal fusion may depend upon several factors. For instance, the spacer—or implant or cage—used to fill the space left by the removed disc and bony anatomy must be sufficiently strong to support the spine under a wide range of loading conditions. The spacer should also be configured so that it is likely to remain in place once it has been positioned in the spine by the surgeon. Additionally, the material used for the spacer should be a biocompatible material and should have a configuration that promotes bony ingrowth.

As a result, the design of the implant should provide sufficient rigidity and strength to resist deformation when loading forces are applied to it. Likewise, the implant should sufficiently resist sliding or movement of the implant as a result of torsional or shearing loads. Often, these parameters lead designers to select predominantly solid structures made of bone or of radio opaque materials such as titanium.

Instrumentation and specialized tools for insertion of an intervertebral implant is yet another design parameter to consider when designing a spacer. Spinal fusion procedures can present several challenges because of the small clearances around the spacer when it is being inserted into position. For instance, the instrumentation used may securely grip the implant on opposing sides or surfaces. For example, the superior and inferior surfaces may have one or more regions in which no gripping teeth are present. Such protrusion-free zones enable the implant to be grasped and manipulated by elongate rectangular blades. Notably, these protrusion-free zones are not formed as channels cut into the surface of the implant in order to maintain the strength and integrity of the implant so that it is less prone to failure. Thus, the clearance required in order to insert the spacer must be higher than the spacer itself in order to accommodate the instrumentation. For this reason, distraction of the treated area typically is greater than the implant itself.

Similarly, when the gripping tools used to manipulate and insert the implant are on the sides of the spacer, additional clearance typically is needed in order to accommodate the added width of the insertion tool blades. Such increases in height or width of the profile of the spacer when coupled or in communication with instrumentation means that additional space is needed in order to insert the spacer. In some circumstances, providing for this additional clearance space can be difficult to achieve.

Thus, despite known devices that promote fusion of a treated area of the spine, there remains a need for spacer designs that optimize bony ingrowth, have structural rigidity to support the spine under a variety of loading conditions, and allow for insertion through a smaller profile.

DETAILED DESCRIPTION OF THE ILLUSTRATED EMBODIMENTS

Embodiments of the present invention are generally directed to implantable spacers that can be used to fuse together a treated area of the spine while restoring or maintaining the proper spacing and natural curvature of the spine. The treated area may include regions between adjacent vertebral bodies so that the height of the spacer corresponds approximately to the height of the disc. In some embodiments, the height of the spacer of may be greater than the height of a disc alone. For instance, the treated area of the spine may be prepared by the physician by removing all or part of at least one vertebral body.

As explained in greater detail below, several features of the invention allow for more efficient insertion or placement of the spacers into a desired position. Additionally, aspects of the invention also provide suitable rigidity and integrity for supporting the spine during fusion while also providing greater ability to confirm that fusion is taking place as desired.

One feature that may result in more efficient insertion or placement of embodiments of spacers according to the invention concerns how the spacers may receive instrumentation for manipulation and insertion of the spacer into its proper position. As mentioned above, conventional tooling for manipulating the spacer generally requires that there be greater clearances in the treated area than needed for the spacer alone in order to accommodate the portions of the tooling that extend beyond the surface of the spacer. In contrast, some embodiments of the present invention do not require an insertion area that is larger than the spacer. Thus, in one embodiment the spacer has one or more tooling engagement surfaces disposed on opposing surfaces of the spacer. The spacer is thereby capable of being manipulated or inserted into position by gripping the engagement surfaces with a suitable tool.

For instance, one example of a suitable gripping tool may be a device having a plurality of arms that may be selectively expanded or opened and subsequently closed or compressed onto the engagement surface. In one embodiment, the engagement surface is formed from plurality of channels formed in the spacer. In one variation, there is a channel located at each engagement surface in which the arms of the manipulating or insertion tool may be disposed to further help ensure that the tooling does not project beyond the largest cross-sectional view of the spacer when viewed along the direction in which the spacer will travel during insertion.

Once the spacer has been moved into position, it is desirable for it to have sufficient structural rigidity or integrity that the spacer does not buckle or otherwise fail under loading by the spine. In general, the spacer should be configured so that it meets requirements for axial compression, axial torsion, subsidence, and resistance to expulsion. As used herein, structural rigidity or integrity refers to the capability of the spacer to resist axial compression and axial torsion without buckling or otherwise failing.

In order to minimize the risk of failure from compressive or torsional loading, it is preferred that the spacer meets or exceeds minimum structural rigidity values. In general, it is preferred that the rigidity of the spacer exceeds the rigidity of the neighboring vertebral bodies to ensure that the spacer does not collapse or fail under loading conditions first. For instance, in one embodiment the spacer is capable of bearing axial compression loads of about 10 kN or more, while in another the spacer is capable of undergoing axial compression loading of about 15 kN or more. In general, increases in rigidity often can lead to larger bulk or size of the spacer. Thus, while the spacer should be sufficiently rigid to withstand expected loading conditions, eventually the benefits of increasing rigidity become outweighed by other disadvantages such as overall size of the spacer or its ability to provide through holes for promoting fusion. For example, in one embodiment, the spacer 30 is capable of bearing axial loads of about 30 kN or less, while in another the spacer is capable of withstanding about 25 kN or less of axial compression. Additionally, these upper and lower limits may be combined in any manner desired. For instance, a spacer of the present invention may be capable of bearing axial compression loads from about 10 kN to about 30 kN, from about 15 kN to about 25 kN, or from about 10 kN to about 25 kN.

Likewise, the spacer may be capable of resisting torsional loading at least to the degree of torsional resistance that a healthy disc could provide. In one embodiment, the spacer is capable of resisting about 1.8 Nm or more of torsional loading. In alternate embodiments, however, the spacer is capable of resisting about 40 Nm or more of torsional loading.

In addition to having structural rigidity or integrity, the spacer should be configured so that it subsides in a desired position without substantially sinking into or piercing nearby anatomy when subjected to axial loading. Different regions of the spine have different sized vertebral bodies, each of which may be subjected to different types and amounts of loading. For instance, vertebral bodies in the lumbar region of the spine are generally larger than vertebral bodies in the cervical region. Typically, the lumbar region of the spine may be subjected to approximately 450 N or more of standing trunk weight, whereas the cervical region may only be subjected to about 50 N of head weight. The larger size of the vertebral bodies in the lumbar region helps distribute the increased loading over a greater area.

The spacer also may be configured to resist threshold amounts of expulsion forces. For example, a normal disc may be capable of resisting shear stresses up to about 150 N. Therefore, the spacer may be configured to withstand at least the same degree of shear loading without moving out of its desired position. More preferably, however, the spacer is capable of withstanding even greater shear stresses. For example, the disc may be capable of withstanding about 600 N or more of shear loading, and in another embodiment it is capable of withstanding about 900 N or more. This feature of the spacer is primarily dependent on the configuration of the protrusions placed on the upper and lower surfaces of the spacer. Thus, the spacer may be configured to withstand even more shear stress, such as loading of about 1000 N or more.

The height of a spacer may be varied depending upon the height of the area of the spine that is to be treated. For this reason, a plurality of spacers having varying heights may be provided to a physician. This allows the physician to select from a variety of spacer heights during a surgical procedure. In one embodiment, the height of the window also increases as the overall height of each spacer increases, which in turn may change or alter the relationship between the area of the window and the area of the blocked by the material forming the spacer. One alternative way to describe the spacer window size is by the span or horizontal width of the window.

Fusion typically is expected to begin in the anterior region of the treated area. One reason for this may be that the anterior region may undergo more axial loading than the posterior region. The additional pressure in this region may trigger fusion to begin. Thus, the lines of sight created by the openings or windows may be positioned so that they intersect in an anterior region of the treated area.

Any biocompatible material may be used to form a spacer of the present invention. For example, suitable materials for forming spacers of the present invention may be include, but are not limited to, titanium and other surgical grade metals and metal alloys. Since metals and metal alloys generally are radio-opaque, several of the advantages of providing large openings or windows in order to view the treated area will be apparent when the spacer is made of these materials. In addition, radiolucent materials also may be used to form spacers of the present invention. For example, either all or a substantial portion of the spacer may be formed of Polyetheretherketone (PEEK) polymers or similar materials. A spacer made of PEEK or other radiolucent material may further comprise a pin disposed within the spacer that helps a physician identify the orientation of the spacer during insertion. Other materials likewise may be used to from all or part of the spacers of the present invention. For example, all or a portion of the spacer may be formed of bioresorbable materials that, over time, may be resorbed and replaced by bone.

These and other features are explained more fully in the embodiments illustrated below. It should be understood that in general the features of one embodiment also may be used in combination with features of another embodiment and that the embodiments are not intended to limit the scope of the invention.

Referring to FIGS. 1-5, one embodiment of a spacer or implant 10 according to the invention comprises a support body 12 and a rotatable insert 14 assembly. Support body 12 may have an arcuate or curved shape extending laterally from a proximal end portion 16 to a distal end portion 18. The distal end 18 portion may have a tapered end 20 narrowing towards the distal most end. In one embodiment, a longitudinal opening 22 may extend through implant 10 to facilitate bone growth through implant 10 and fusion when implanted. A plurality of protrusions or teeth 24 may be provided along the superior and inferior end surfaces to facilitate prevention of expulsion of implant 10 from between the adjacent vertebral bodies between which it may be implanted.

Figure 4A:
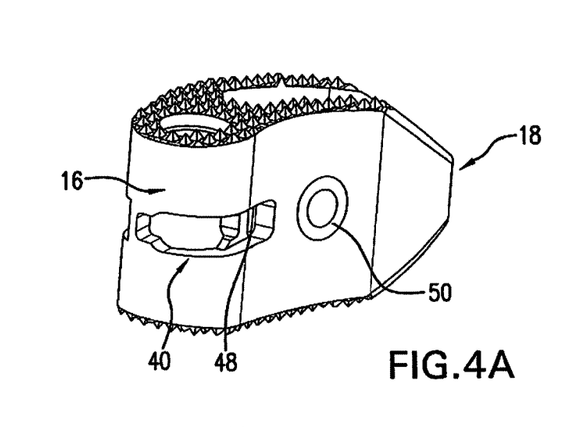
FIGS. 4A-4D are perspective views of a support body of the implant of FIGS. 1-3
FIGS. 5A-5D are top, rear, side, and front views, respectively, of the support body FIGS. 1-4.
Figure 4B:
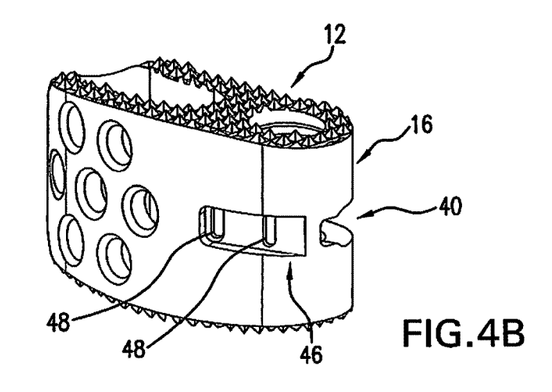
Figure 4C:
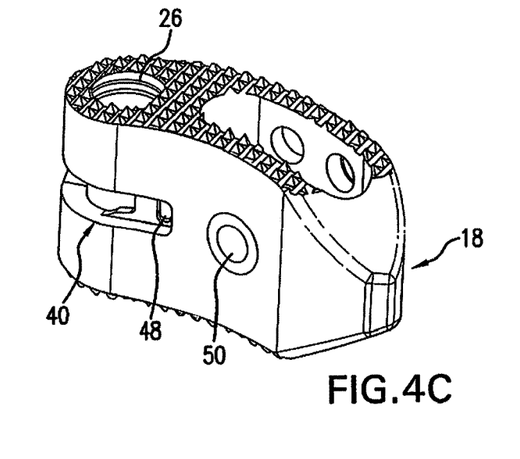
Figure 4D:
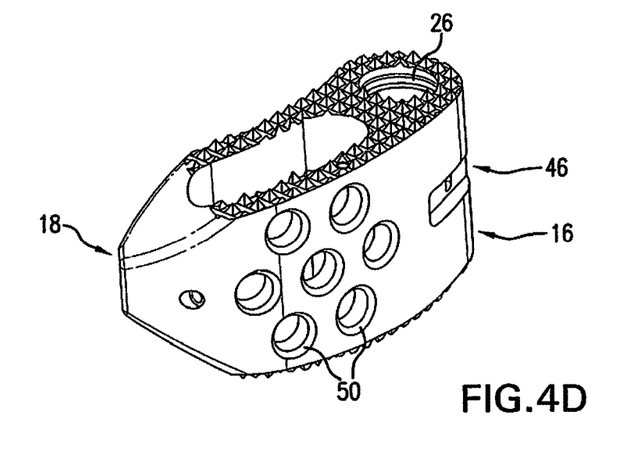
Figure 5A:
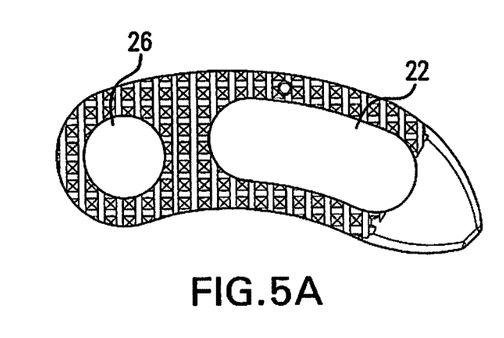
Figure 5B:
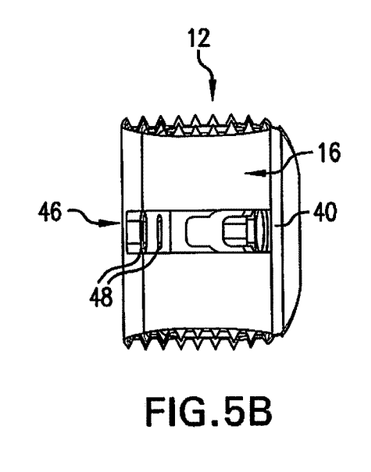
Figure 5C:
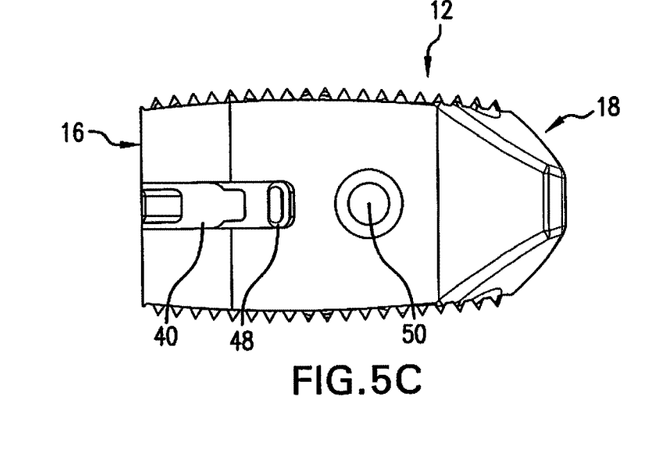
Figure 5D:
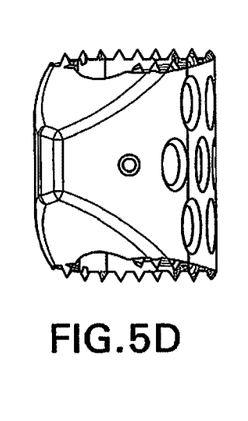

In one variation a longitudinal hole 26 may be provided to accommodate insert 14. In this regard, hole 26 may be configured and dimensioned to receive insert 14 and permit rotational movement between insert 14 and support body 12. In one variation, insert 14 has a cylindrical shape and allows the implant 10 to turn freely when desired but may be locked, fixed, or stabilized in a predetermined position by insertion tool 28. For example, the position may be locked for initial insertion by a sleeve, holder, or stabilization member. According to one embodiment, insert 14 may be captured within hole 26 of support body 12 by a circumferential rib 32 on the insert 14 that mates to a corresponding indentation shaped on the support body 12. In this regard, once assembled, insert 14 is generally constrained longitudinally with respect to support body 12. Insert 14 may have a threaded hole 34 therein extending transverse to longitudinal axis 36 to interface with insertion tool 28. An indention, marking or other alignment mechanism 37 may be aligned with hole 34 and may be provided in the superior surface of insert 14 so that a user may visually align the hole 34 with an opening in the proximal end 16 of implant 10. A slot 38 may be provided adjacent the threaded hole 34 to provide counter-torque and or stabilization to insert 14 and to facilitate threaded insertion of the insertion instrument 28 with the insert 14. In one variation, slot 38 runs generally perpendicular to threaded hole 34. As shown in FIGS. 1, 4A-D, and 5B, the proximal end portion 16 of implant 10 may have a rounded shape and may include one or more slots or grooves 40, 46 to engage insertion instrument 28 to facilitate insertion of spacer 10. In one embodiment, groove 40 extends adjacent the proximal end and extends along the interior curved wall of support body 12. Groove 40 has an opening in communication with hole 26 to allow a part of insertion tool 28 to engage threaded hole 34. For example, in one variation insertion tool 28 may include a shaft 42 with a threaded tip portion 44 to threadedly engage insert 14. As shown in FIG. 4B another slot 46 may be provided adjacent the outer curved wall of support body 12. One or more indentations 48 may be provided within groove 46 to accommodate protrusions on insertion tool to enhance gripping of the insertion tool 28 with spacer 10.

Figure 1:
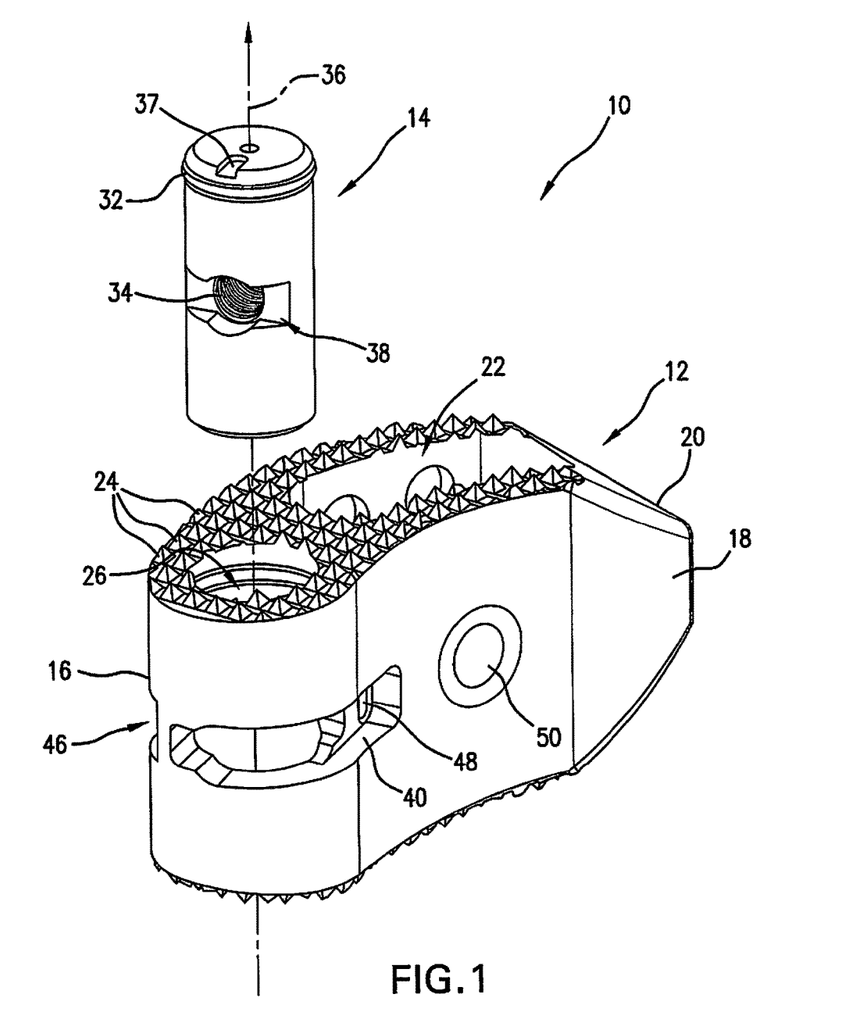
FIG. 1 is a perspective exploded view of one embodiment of an implant according to the invention.
Figure 2:
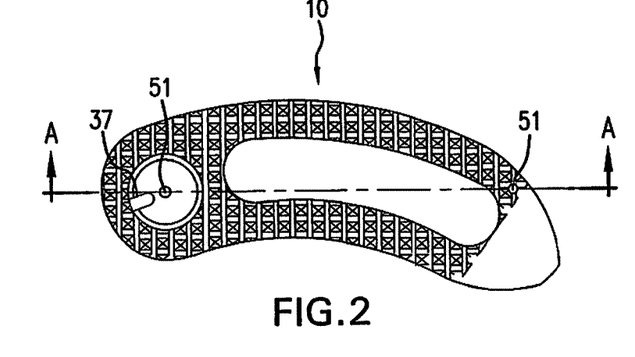
FIG. 2 is a top view of an assembled implant of the embodiment of FIG. 1.
Figure 3:
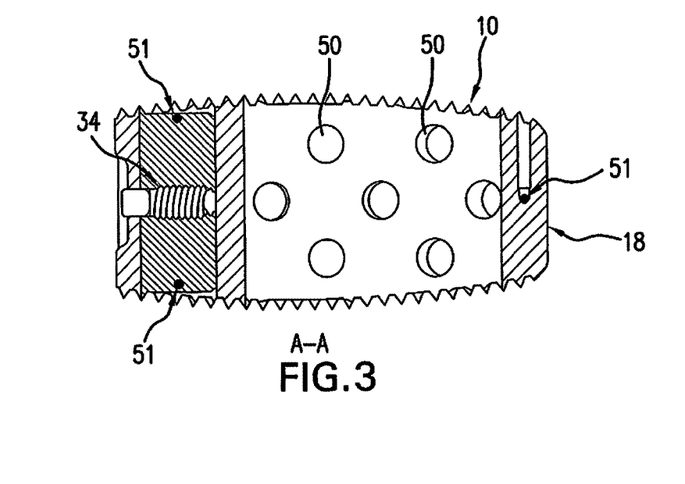
FIG. 3 is a cross-sectional view of the implant of FIG. 2 taken along the line A-A.

One or more openings 50 may be provided extending through the curved side walls and into the central longitudinal opening 22. Openings 50 may facilitate bony ingrowth and may provide a window through which bony fusion may be visually confirmed. As best seen in FIGS. 2-3, when implant 10 is made from radiolucent material such as PEEK, one or more radio-opaque markers 51 may be integrated into implant 10 such that the implant may be viewed and or located when using fluoroscopy.

Figure 6:
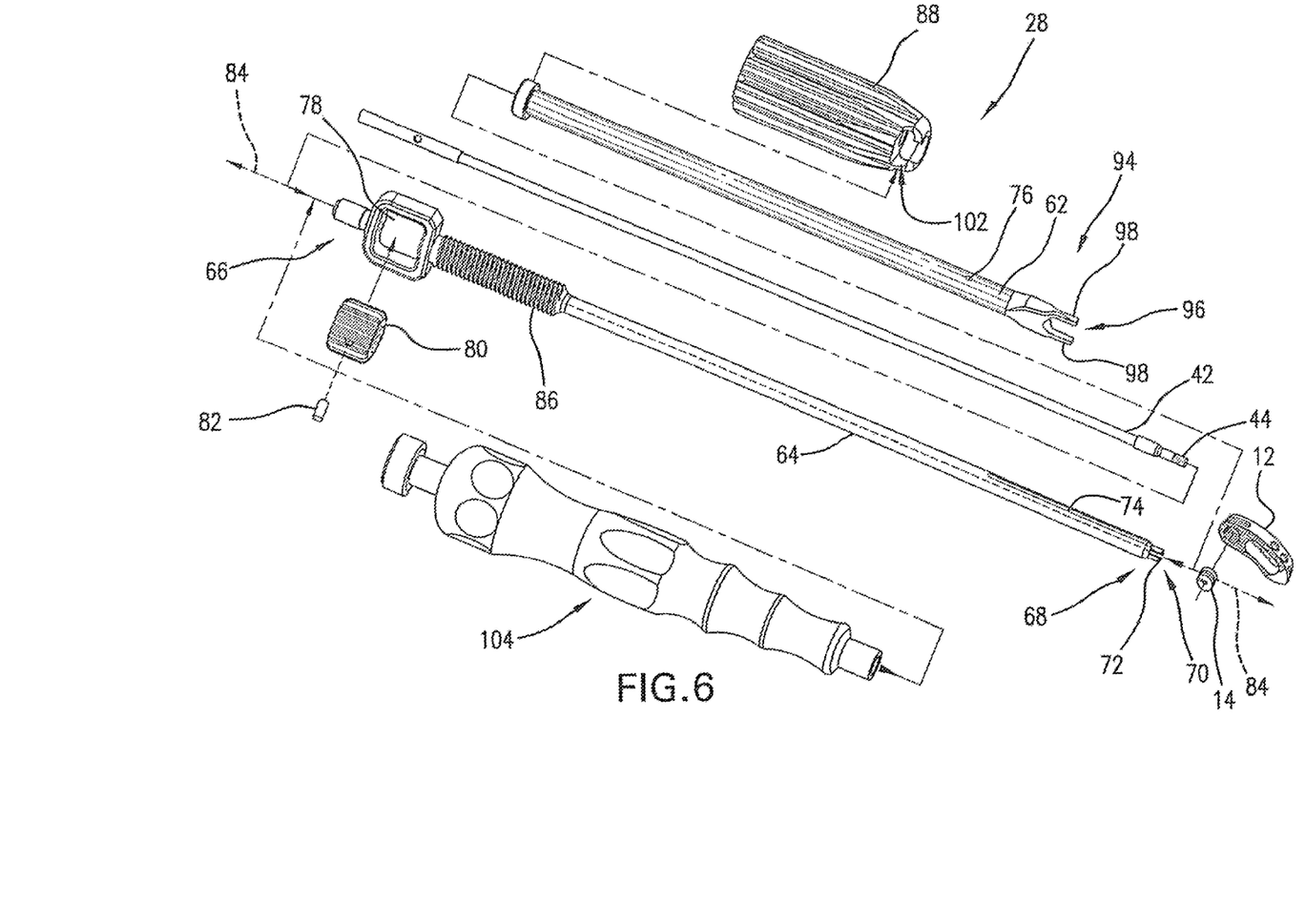
FIG. 6 is an exploded view of one embodiment of an insertion instrument according to the invention.
Figure 7:
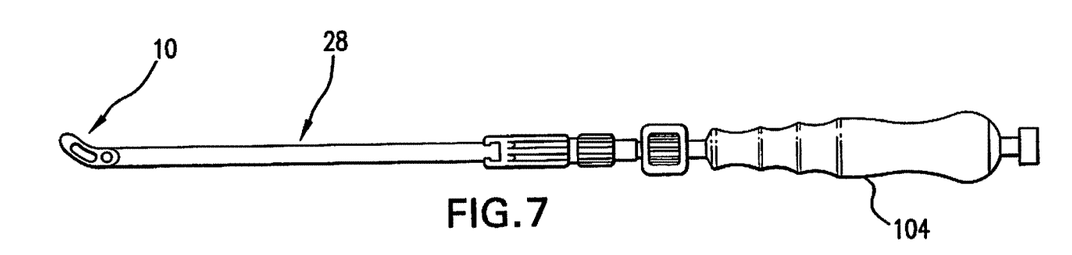
FIG. 7 is an assembled view of the instrument of FIG. 6 having an implant of FIG. 1 attached thereto.

Referring to FIG. 6, an exploded view of one embodiment of an insertion instrument 28 according to the invention is shown. Instrument 28 generally comprises an implant stabilizer 62, an insert stabilizer 64, and a central shaft 42 extending through the implant and insert stabilizers 62, 64. As explained above, central shaft 42 has a threaded distal tip portion 44 to threadedly engage insert 14. Insert stabilizer 64 may have a generally cylindrical body extending from a proximal end 66 to a distal end 68. Insert stabilizer 64 is cannulated to accommodate central shaft 42 therethrough. In one variation, distal end 68 of insert stabilizer 64 has a forked free end 70 with a pair of tongs or prongs 72 spaced apart and extending distally therefrom. The prongs 72 are configured and dimensioned to engage slot 38 of insert 14. A keyed slot 74 may be provided adjacent the distal end 68 and extending proximally therefrom. Keyed slot 74 is generally configured and dimensioned to engage and interface with a pin 76 provided in implant stabilizer 62. The proximal end 66 of insert stabilizer 64 may have an opening 78 extending transversely therethrough configured and dimensioned to receive a rotatable wheel or thumbwheel 80. Thumbwheel 80 has a central opening configured to receive central shaft 42 therethrough and a set screw 82 may extend through the thumbwheel 80 to axially and rotationally fix central shaft 42 to thumbwheel 80 so as to rotationally constrain central shaft 42 to thumbwheel 80. In this regard, in operation a surgeon utilizing the installation instrument 28 may rotate the central shaft 42 by rotating the thumbwheel 80 about axis 84. An externally threaded region 86 may be provided adjacent opening 78 to interface or otherwise engage an internally threaded stabilizer lock wheel 88.

Figure 8:
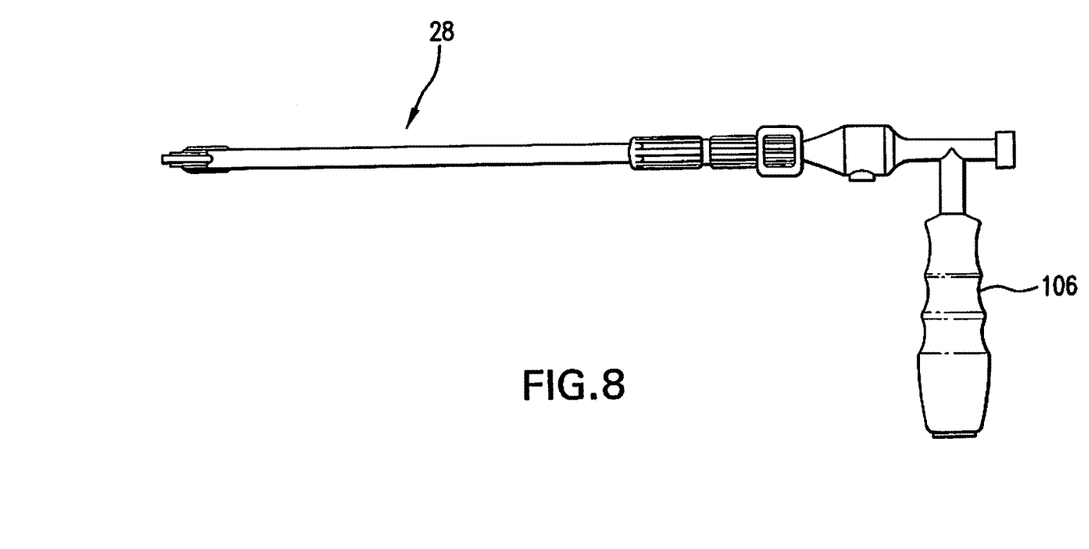
FIG. 8 is an assembled view of an alternate embodiment of an instrument according to the invention.

Implant stabilizer 62 may be a generally cylindrical cannulated body extending from a proximal end 92 to a distal end 94 configured and dimensioned to extend over insert stabilizer 64. In one variation, distal end 94 of implant stabilizer 62 has a forked free end 96 with a pair of tongs or prongs 98 spaced apart and extending distally therefrom. Prongs 98 are configured and dimensioned to engage the slots or grooves 40, 46 of implant 12. A flange or shoulder 100 may be provided adjacent proximal end 92 and flange 100 may engage a slot 102 in stabilizer lock wheel 88 to constrain axial movement between the implant stabilizer 62 and stabilizer lock wheel 88 yet allow rotational movement therebetween. In this regard, as stabilizer lock wheel 88 is rotated about threaded region 86, the distal end 94 of implant stabilizer 62 may be advanced or moved along axis 84 to engage the slots 40, 46 on implant 10 so as to stabilize implant 10 with respect to prongs 98. With prongs 98 engaged with slots 40, 46, implant 10 is rigidly attached to instrument 28 and locked rotationally such that implant 10 is prevented from being rotated or articulated with respect to insertion tool axis 84. Those skilled in the art may appreciate the desirability of such a feature when, for example, the spacer may be hammered or impacted into place between adjacent vertebrae. In this regard, the surgeon user may apply axial force on the insertion tool axis without risk that such impaction will cause the spacer to rotate or articulate with respect to axis 84. If and when the surgeon user desires to allow the implant to articulate with respect to axis 84, he may disengage the implant stabilizer 62 from the implant to selectively allow the implant to articulate with respect to axis 84. In one variation, an ergonomic handle 104 may be connected to the proximal end 92 of instrument 28 to facilitate handling and/or impaction. Referring to FIG. 8, in an alternate embodiment an alternate T-shaped handle 106 may be connected to proximal end 92 of instrument 28. Those skilled in the art may appreciate that such a T-shaped handle may facilitate, among other things, enhanced visibility of the surgical site by a surgeon user.

Figure 9:
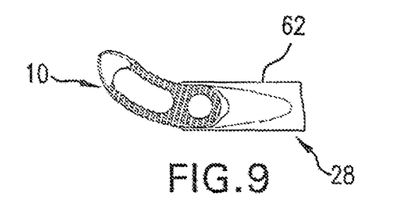
FIGS. 9-12 are views depicting the articulation of the implant of FIG. 1 with respect to installation instruments according to the invention.
Figure 10:
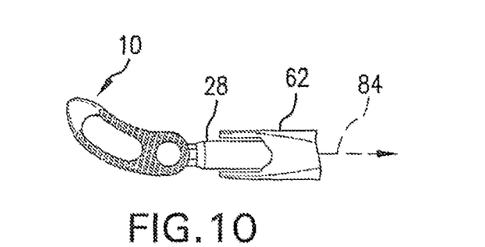
Figure 11:
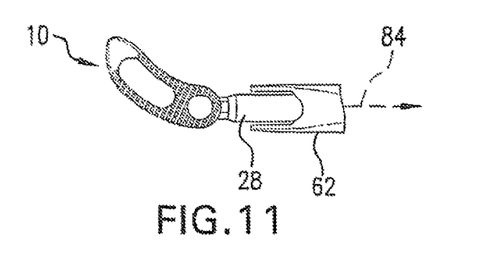
Figure 12:
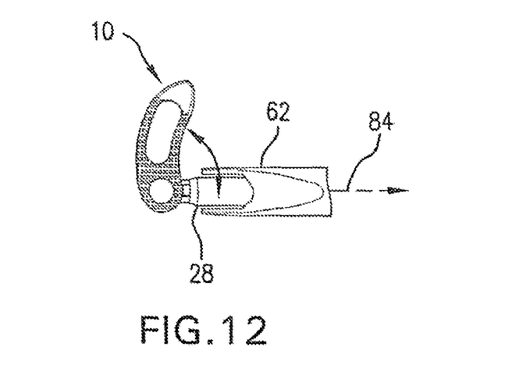
Figure 13:
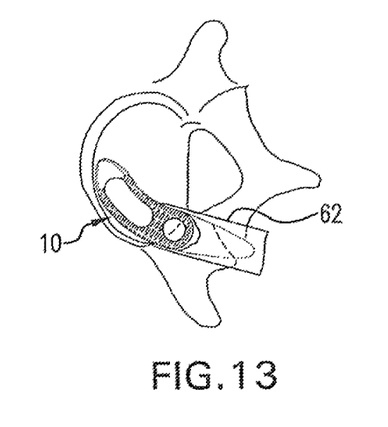
FIGS. 13-16 are views showing the placement of an implant of the invention between vertebral bodies using an instrument of the invention.

Referring now to FIGS. 9-12, the articulatability of implant 10 with respect to installation instrument 28 is shown. As shown in FIG. 9, implant stabilizer 62 is engaged on implant 10 so as to stabilize implant 10 and/or rigidly attach to instrument 28. In this position, implant 10 is locked rotationally such that it is prevented from being rotated or articulated with respect to insertion tool axis 84. In one variation, shown in FIG. 9, implant 10 may extend in a generally axial direction along axis 84 from the end of tool 28. Referring to FIGS. 10-12, with implant stabilizer 62 disengaged from implant 10, the implant is free to rotate or articulate with respect to axis 84 of insertion tool 28. In one variation, implant 10 may articulate or rotate between about 0 degrees (FIG. 10) and about 90 degrees (FIG. 12).

Referring now to FIGS. 13-16, one embodiment of a method of using implant 10 in conjunction with inserter 28 is shown. In a first step, the implant 10 may be threadedly engaged onto insertion tool 28 using thumbwheel 80 to rotate central shaft 42 and threadedly engage the threaded distal tip portion 44 into threaded hole 34 of insert 14. The stabilizer lock 88 may then be turned clockwise to engage implant stabilizer prongs 98 with slots 40, 46 on implant 10 to prevent implant 10 from rotating about insertion tool axis 84. In this position, with the implant 10 fixed or stabilized with respect to the insertion instrument 28, the insertion tool 28 may be impacted from the proximal end. For instance according to one method shown in FIG. 13, a surgeon may impact the proximal end of handle 104 to achieve a desired positioning or depth between adjacent vertebral bodies using, for example, a transforaminal approach. As explained above, the surgeon user may apply axial force on the insertion tool axis without risk that such impaction will cause the implant to rotate with respect to axis 84. The tapered distal end 20 of implant 10 may facilitate distraction separation or spreading apart of the adjacent vertebral bodies. A counter lock may be provided on the installation instrument to prevent stabilizer lock 88 from moving and to prevent implant stabilizer 62 from disengaging from implant 10 during impaction.

Figure 14:
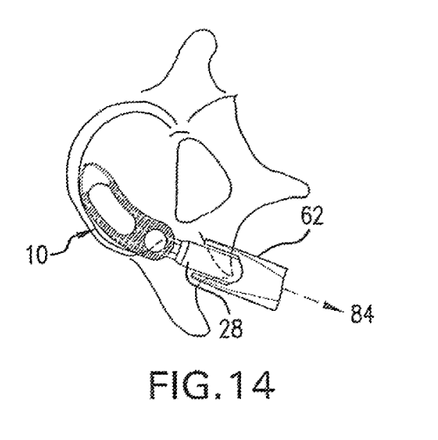
Figure 15:
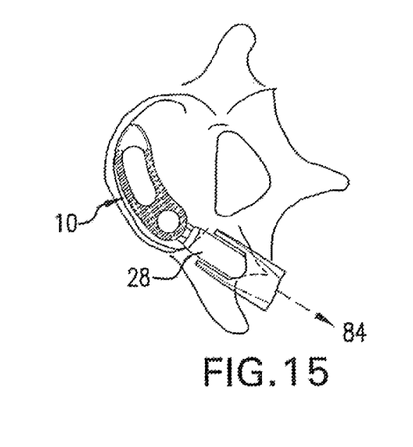
Figure 16:
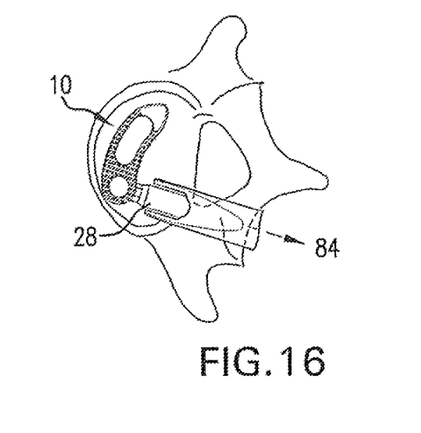

Referring to FIG. 14, once impacted to a desired position, the implant 10 may be released from the implant stabilizer 62 by turning the stabilizer lock counterclockwise and retracting stabilizer 62 axially to disengage prongs 98 from slots 40, 46. With the implant stabilizer 62 released the implant 10 is free to articulate at the end of insertion tool 28. In this regard, in this position support body 12 may rotate about insert 14 and a central rotation axis 36 extending through the center of insert 14. Referring to FIGS. 15-16, once the stabilizer 62 is released a surgeon may impact the instrument further to advance the implant 10 into the intervertebral space. In this regard, the outer sidewall of distal end 16 of support body 12 is configured and dimensioned to contact or otherwise engage the epiphyseal ring on an anterior portion of a vertebral disc to provide force on the distal end 16 causing implant 10 to rotate in-situ in the intervertebral space about the axis of rotation 36. In certain methods, such rotation may accompany axial translation of axis 36 toward the anterior portion of the disc space, for example, upon impaction of installation instrument 28. Referring to FIG. 16, according to one method, implant 10 may reach a desired or final installation or implantation position wherein implant 10 is positioned adjacent the epiphyseal ring along the anterior portion of the disc space. Once the desired or final installation position of implant 10 is reached, the insertion instrument 28 may be released from implant 10 by unthreading the connection between insertion instrument 28 and insert 14 and insertion instrument 28 may be removed from the body. In this regard, implant 10 and insert 14 are configured and dimensioned to remain implanted in the patient.

Figure 17:
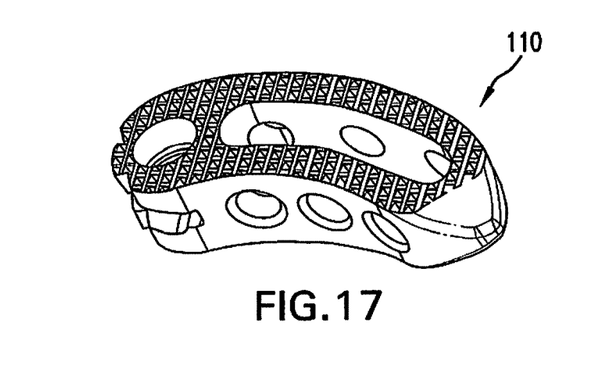
FIGS. 17-18 are side perspective views of alternative embodiments of implants.
Figure 18:
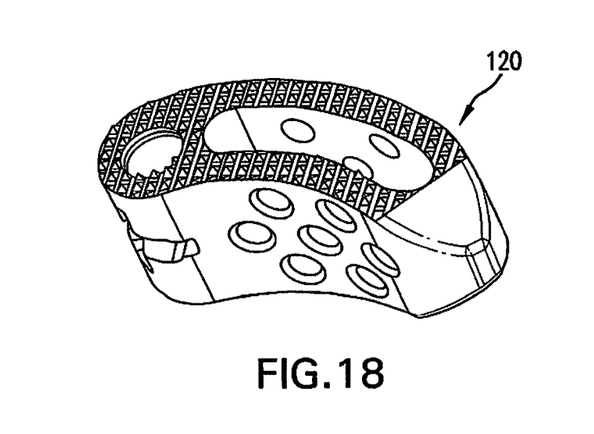

Referring to FIGS. 17-18, alternative embodiments of implants 110 and 120 according to the invention are shown.

While it is apparent that the invention disclosed herein is well calculated to fulfill the objects stated above, it will be appreciated that numerous modifications and embodiments may be devised by those skilled in the art.

We claim:

1. An assembly for implant installation between adjacent vertebral bodies of a patient, comprising:
    an implant having a support body and a rotatable insert therein;
    the support body having a first curved side extending laterally from a proximal end portion to a distal end portion and the support body is configured and dimensioned for installation between adjacent vertebral bodies transforaminally;
    wherein the support body includes a superior surface and an inferior surface, wherein the superior surface and inferior surface include a plurality of protrusions to facilitate prevention of expulsion of the implant once installed, and
    wherein the support body defines a first longitudinal opening extending longitudinally therethrough from the superior surface to the inferior surface and defines at least one opening on the first curved side extending into the longitudinal opening;
    wherein the support body defines a second longitudinal opening extending therethrough from the superior surface with protrusions to the inferior surface with protrusions and positioned in between the proximal end and the distal portion to accommodate the rotatable insert therein and wherein the insert is rotatable about a central longitudinal axis within the second longitudinal opening to permit the support body to rotate about the insert and the central longitudinal axis; and
    an installation instrument removably attached to the proximal end portion of the support body and engageable with the rotatable insert to selectively permit rotation between the insert and the support body, the installation instrument extending along a longitudinal tool axis,
    wherein when the installation instrument is in a first position the insert is rotationally fixed with respect to the support body and when the installation instrument is in a second position the support body may rotate with respect to the insert
    wherein a circumferential rib is provided on the insert and a correspondingly shaped indentation is provided on the support body and the insert is captured within the second longitudinal opening of the support body when the insert is inserted therein.

2. The assembly of claim 1, wherein when the installation instrument is in the first position a sleeve of the installation instrument engages a slot formed in the proximal portion of the support body.

3. The assembly of claim 1, wherein the insert defines a threaded hole extending transverse to the central longitudinal axis to engage with the installation instrument.

4. The assembly of claim 1, further comprising an alignment member in a superior surface of the insert aligned with the hole.

5. The assembly of claim 1, wherein the proximal end portion has a rounded shape and includes one or more grooves on lateral sides of the implant to engage installation instrument and wherein the grooves are in communication with the second longitudinal opening to allow a part of insertion tool to engage the rotational insert.

6. The assembly of claim 1, wherein the installation instrument includes a central shaft having a threaded tip portion for threaded engagement with the rotatable insert.

7. The assembly of claim 6, wherein the installation instrument comprises an implant stabilizer configured and dimensioned to engage the support body, an insert stabilizer configured and dimensioned to engage the rotatable insert, and wherein the central shaft extends through the implant and insert stabilizer.

8. The assembly of claim 7, wherein the implant stabilizer has a generally cylindrical body extending from a proximal end to a distal end, and wherein the distal end comprises a forked free end having a pair of tongs spaced apart and extending distally therefrom and the tongs are configured and dimensioned to engage the one or more grooves of the implant to stabilize the implant with respect to the tongs and prevent rotation of the support body with respect to the longitudinal tool axis.

9. The assembly of claim 1, wherein the second longitudinal opening is surrounded at least in part by one or more protrusions.

10. The assembly of claim 1, wherein the support body further includes a groove that extends adjacent the proximal end portion and extends along an interior curved wall of the support body.

11. The assembly of claim 1, wherein the installation instrument comprises an implant stabilizer and an insert stabilizer.

12. A method for implant installation between adjacent vertebral bodies of a patient, comprising the steps of:
    assembling an implant onto an insertion tool;
    the implant having a support body and a rotatable insert therein;
    the support body having a plurality of radiopaque markers;
    wherein the support body includes a superior surface and an inferior surface, wherein at least one of the superior surface and inferior surface include a plurality of protrusions to facilitate prevention of expulsion of the implant once installed, and
    wherein the support body defines a first longitudinal opening extending longitudinally therethrough from the superior surface to the inferior surface;
    wherein the support body defines a second longitudinal opening extending therethrough from the superior surface with protrusions to the inferior surface with protrusions and positioned in between the proximal end and the distal portion to accommodate the rotatable insert therein and
    wherein the insert is rotatable about a longitudinal axis within the second longitudinal opening to permit the support body to rotate about the insert and the longitudinal axis;
    the installation instrument extending along a longitudinal tool axis;
    moving the installation instrument to a first position wherein the insert is rotationally fixed with respect to the support body and the implant is rotationally fixed with respect to the longitudinal tool axis;
    placing the implant into a patient through a transforaminal approach to locate the implant between adjacent vertebral bodies of a patient;
    advancing the implant between the adjacent vertebral bodies into an intervertebral space therebetween;

moving the installation instrument to a second position wherein the support body is rotatable with respect to the insert;

advancing the implant further into the intervertebral space such that the implant rotates with respect to the longitudinal tool axis.

13. The method of claim 12, wherein the distal end of the implant is tapered separates the adjacent vertebral bodies when the installation instrument is in a first position and the implant is advanced into the intervertebral space.

14. The method of claim 12, wherein a lock is provided on the installation instrument to prevent the instrument from disengaging from the implant during impaction.

15. The method of claim 12, wherein the implant and insert remain implanted in the patient.

16. An assembly for implant installation between adjacent vertebral bodies of a patient, comprising:

an implant having a support body and a rotatable insert therein;

the support body having a first curved side extending laterally from a proximal end portion to a distal end portion and the support body is configured and dimensioned for installation between adjacent vertebral bodies transforaminally;

wherein the support body includes a superior surface and an inferior surface, wherein the superior surface and inferior surface include a plurality of protrusions to facilitate prevention of expulsion of the implant once installed, and wherein the support body defines a first longitudinal opening extending longitudinally therethrough from the superior surface to the inferior surface and defines at least one opening on the first curved side extending into the longitudinal opening;

wherein the support body defines a second longitudinal opening extending therethrough from the superior surface with protrusions to the inferior surface with protrusions and positioned in between the proximal end and the distal portion to accommodate the rotatable insert therein and wherein the insert is rotatable about a central longitudinal axis within the second longitudinal opening to permit the support body to rotate about the insert and the central longitudinal axis; and an installation instrument removably attached to the proximal end portion of the support body and engageable with the rotatable insert to selectively permit rotation between the insert and the support body, the installation instrument extending along a longitudinal tool axis, wherein when the installation instrument is in a first position the insert is rotationally fixed with respect to the support body and when the installation instrument is in a second position the support body may rotate with respect to the insert, wherein the insert includes a circumferential rib that mates to a corresponding indentation shaped on the support body.

* * * * *